United States Patent [19]

Kita et al.

[11] 4,141,813
[45] Feb. 27, 1979

[54] OXYGEN SENSOR PARTICULARLY USEFUL IN EXHAUST SYSTEM OF AUTOMOTIVE ENGINE

[75] Inventors: Toru Kita; Takeshi Fujishiro, both of Yokohama, Japan

[73] Assignee: Nissan Motor Company, Limited, Yokohama, Japan

[21] Appl. No.: 769,350

[22] Filed: Feb. 16, 1977

[30] Foreign Application Priority Data

Feb. 19, 1976 [JP] Japan .................................. 51-16560

[51] Int. Cl.$^2$ ............................................ G01N 27/46
[52] U.S. Cl. ................................................. 204/195 S
[58] Field of Search ............................. 204/1 S, 195 S

[56] References Cited

U.S. PATENT DOCUMENTS

| | | |
|---|---|---|
| 3,468,780 | 9/1969 | Fischer .............................. 204/195 S |
| 3,616,407 | 10/1971 | Engell et al. ..................... 204/195 S |
| 3,773,641 | 11/1973 | Fitterer ............................. 204/195 S |
| 3,791,953 | 2/1974 | Minushkin et al. .............. 204/195 S |
| 3,844,920 | 10/1974 | Burgett et al. ................... 204/195 S |
| 3,960,693 | 6/1976 | Weyl et al. ....................... 204/195 S |
| 4,019,974 | 4/1977 | Weyl et al. ....................... 204/1 S |

FOREIGN PATENT DOCUMENTS 1191222  5/1970  United Kingdom ................. 204/195 S Primary Examiner—T. Tung Attorney, Agent, or Firm—Richard L. Schwaab

[57] ABSTRACT

A solid electrolyte tube closed at one end and two porous electrode layers respectively coated on the outer and inner surfaces of the electrolyte tube constitute a known oxygen concentration cell. A tubular metal shell encloses the electrolyte tube partly such that a closed end portion of the tube protrudes from the shell and that the outer electrode coating is locally in contact with the inside of the shell. To protect the open end of the electrolyte tube against splashing of water during use without interrupting the admission of atmospheric air as a reference gas into the inside of the electrolyte tube, a tubular cap member of a metal is coaxially fixed to and electrically connected at its one end to the shell at one end portion surrounding the open end of the electrolyte tube, and a cross-sectionally circular plug of an insulating material is coaxially and tightly received in and fixed to the cap member to occupy an end portion, contiguous to the free end, of the interior of the cap member. This plug has two axial bores which respectively allow two cable wires of the sensor to tightly pass therethrough and an air-admitting passage formed therein independently of these two bores in such an arrangement and cross-sectional area that unpressurized water does not pass therethrough from the atmosphere to the unoccupied portion of the interior of the cap member.

14 Claims, 20 Drawing Figures

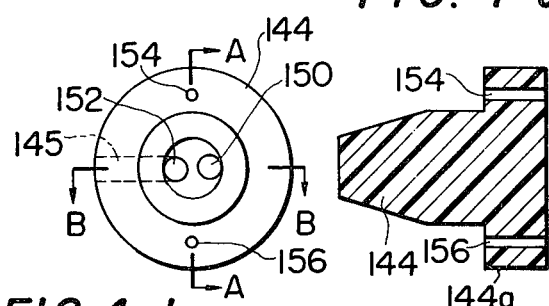
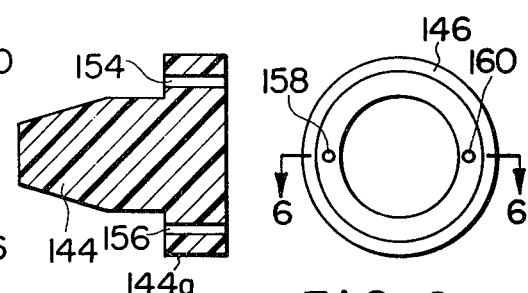
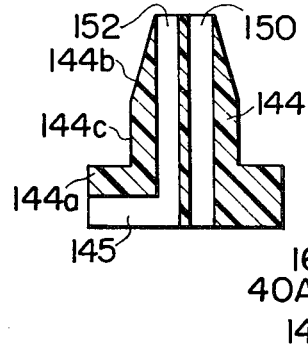
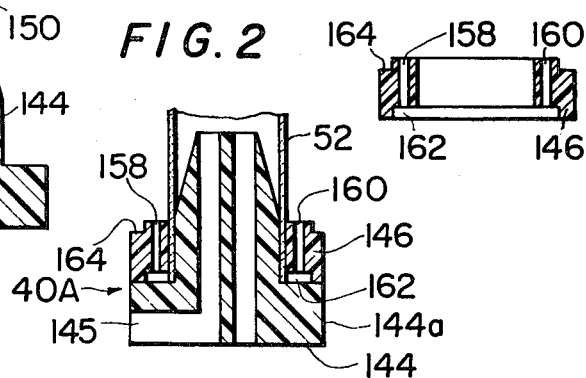
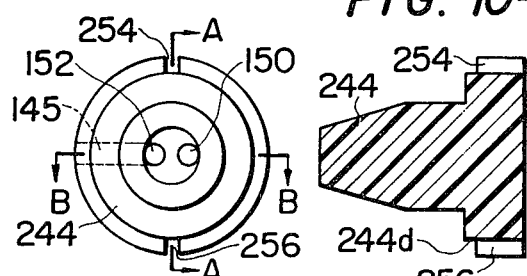
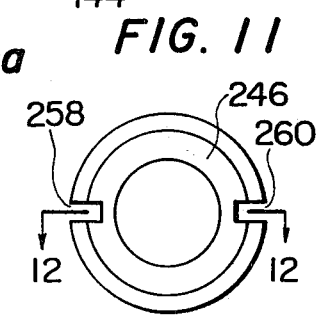
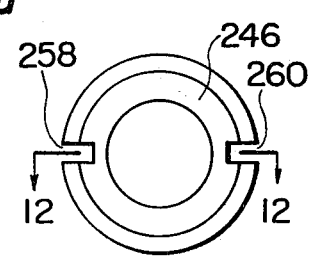
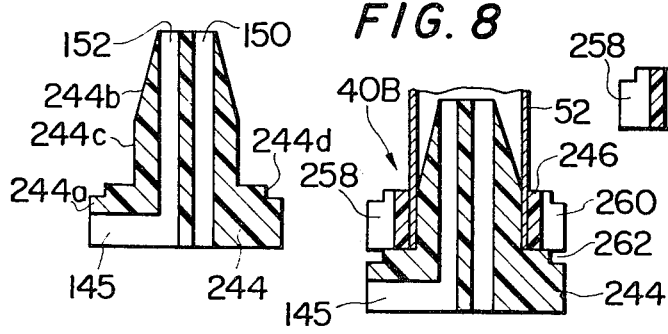
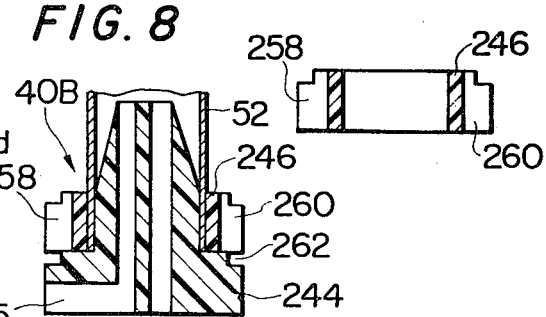

OXYGEN SENSOR PARTICULARLY USEFUL IN EXHAUST SYSTEM OF AUTOMOTIVE ENGINE

BACKGROUND OF THE INVENTION

This invention relates to an oxygen sensor which utilizes an oxygen ion conductive solid electrolyte in the form of a tube closed at one end and has a construction particularly suitable for detecting oxygen concentration in exhaust gas of automotive engines.

An oxygen sensor which has a layer of an oxygen ion conductive solid electrolyte such as stabilized zirconia and operates on the principle of an oxygen concentration cell is well known. This type of oxygen sensor is suitable for detecting oxygen concentration in hot gases, particularly in exhaust gas of internal combustion engines for, chiefly, automotive use as an element of a feedback control system for controlling the air-fuel ratio of a combustible mixture fed to the engines.

In practical applications of this type of oxygen sensors to exhaust systems of internal combustion engines, the solid electrolyte layer in most cases is formed into the shape of a tube which is closed at one end for convenience of attachement to, for example, exhaust pipes for the engines and exposure of one side of the solid electrolyte layer to the exhaust gas and the opposite side to the atmospheric air which serves as a reference gas. The outer and inner surfaces of the solid electrolyte tube are coated with porous (permeable to gases) and electron conductive layers of a metal such as platinum respectively as anode and cathode electrodes of the oxygen concentration cell. This electrolyte tube is tightly inserted into a tubular metal shell such that a closed end portion of the tube protrudes from the shell. This shell has on its outside an attachment means such as screw threads for attachement of the sensor to, for example, a boss formed on an exhaust pipe. Besides, the shell serves as an anode conductor. A tubular metal member is inserted into the solid electrolyte tube from its open end to serve both as a cathode conductor and as an air admission conduit. One of a pair of leads is connected to the anode conductor while the other is connected to either the shell or a cap member (having an air inlet opening) attached to the shell.

When the closed end portion of the electrolyte tube of this sensor is exposed to an exhaust gas stream in the exhaust pipe and the inside of the tube is exposed to the atmospheric air, an electromotive force is developed across the anode and cathode electrodes. The magnitude of this electromotive force varies according to the concentration of oxygen in the exhaust gas relative to the oxygen concentration in air.

The concentration cell of this sensor has a considerably high internal impedance particularly when the electrolyte tube is not sufficiently heated. For example, the internal impedance is above 10 MΩ at cold starting of the engine. To accurately pick up the developed electromotive force even when the sensor is operated at low temperatures, it is important to maintain very high insulation resistances both between the anode and cathode electrodes and between the leads.

A problem encountered by this oxygen sensor, particularly when the sensor is used in automobiles, is splashing of water on the sensor. Since the sensor in an automobile is attached to either the exhaust pipe or an exhaust manifold and the inside of the electrolyte tube is exposed to the atmosphere, the sensor is frequently splashed with water particularly at the open end portion of the electrolyte tube. The splashing of water causes the aforementioned insulation resistances to lower. Furthermore, the electrolyte tube is liable to crack when splashed with water in a heated state. (The temperature of the electrolyte tube, even at its open end portion located outside of the exhaust pipe, reaches to about 300° C. during a continuous operation of the engine.)

To protect the electrolyte tube against splashing of water, it has been proposed to cover the open end of the electrolyte tube with a ceramic disk supported by a cap member attached to the shell of the sensor. However, the provision of this ceramic disk cannot perfectly prevent the inside of the electrolyte tube and/or the joints between the leads and the conductors from being wetted with water, because the cap member has an air inlet opening.

SUMMARY OF THE INVENTION

It is an object of the present invention to solve the above described problem encountered by conventional oxygen sensors of the described type.

It is another object of the invention to provide an improved oxygen sensor which has an improved resistance to splashing of water and hence can long and reliably be used in exhaust lines of automotive engines.

It is a still another object of the invention to provide an improved oxygen sensor which utilizes a solid electrolyte tube with a closed end and an open end like conventional oxygen sensors and has an improved closure plug assembly for covering the open end of the electrolyte, which plug assembly can admit therethrough the atmospheric air as a reference gas to the inside of the electrolyte tube but effectively protects not only the inside and the open end of the electrolyte tube but also a joint between a cathode lead of the sensor and the inside of the electrolyte tube against splashing of external water.

An oxygen sensor according to the invention has (a) an oxygen ion conductive solid electrolyte tube which is closed at one end; (b) anode and cathode electrode layers porously coated on the outer and inner surfaces of the electrolyte tube, respectively; (c) a metal tube which is inserted into the bore of the electrolyte tube to locally be in contact with the cathode electrode layer and serves both as a cathode conductor and as a conduit for admitting air as a reference gas into the interior of the electrolyte tube; and (d) a tubular metal shell which encloses therein a portion of the electrolyte tube such that a closed end portion of the tube protrudes from the shell and that the anode electrode layer is locally in contact with the inside of the shell. The sensor further comprises (e) a tubular cap member of a metal which is coaxially fixed to and electrically connected at its one end to the shell at an end portion surrounding the open end of the electrolyte tube; (f) a pair of lead wires introduced into the interior of the cap member through its free end and respectively connected to the inside of the cap member and the cathode conductor; and, as a primary feature of the invention, (g) a cross-sectionally circular plug of an electrically insulating material coaxially and tightly received in the cap member to occupy an end portion, which is contiguous to the free end, of the interior of the cap member, which plug has two axial bores formed therein to respectively allow the lead wires to tightly pass therethrough and an air-admitting passage formed therein independently of the two bores to provide fluid communication between the unoccupied portion of the interior of the cap member and the atmosphere. The air-admitting passage is arranged and sized in cross section such that unpressurized water does not pass through this passage from the atmosphere to the interior of the cap member.

In this oxygen sensor, at least a major part of the air-admitting passage may be formed in the plug to be isolated from the inner surface of the cap member. Alternatively, the air-admitting passage may be formed along the outer cylindrical surface of the plug to partly be defined by the inner surface of the cap member. In either case, the air-admitting passage is preferably made turning within the plug to surely cause water intruded into the passage to stagnate therein.

As an optional element, the oxygen sensor may further comprise a sheath of a flexible and electrically insulating material, which covers the lead wires at their portions extending outwards from the plug together with an end portion of the plug where the two bores for the lead wires open to the atmosphere. In this case, the air-admitting passage is usually arranged to open to the atmosphere on the outside of the sheath. However, it is also possible to form the air-admitting passage as a hole of a small cross-sectional area which generally axially passes through the entire length of the plug with short distances from the two bores and opens to the interior of the sheath.

BRIEF DESCRIPTION OF THE DRAWINGS

FIG. 2 is a longitudinal sectional view of a plug assembly in the sensor of FIG. 1;

FIG. 3 is a plan view of an element of the plug assembly of FIG. 2;

FIGS. 4-a and 4-b are sectional views respectively taken along the lines A—A and B—B of FIG. 3;

FIG. 5 is a plan view of another element of the plug assembly of FIG. 2;

FIG. 6 is a sectional view taken along the line 6—6 of FIG. 5;

FIG. 8 is a longitudinal sectional view of a differently constructed plug assembly as an alternative to the plug assembly of FIG. 2;

FIGS. 9, 10-a, 10-b, 11 and 12 correspond to FIGS. 3, 4-a, 4-b, 5 and 6, respectively, and show details of the plug assembly of FIG. 8;

DESCRIPTION OF PREFERRED EMBODIMENTS

Figure 1:
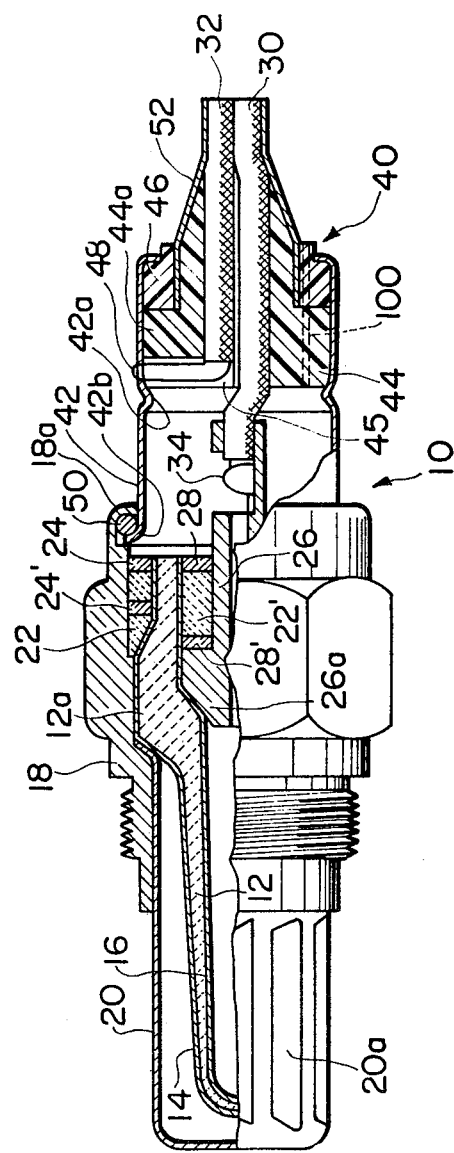
FIG. 1 is a longitudinal sectional view of an oxygen sensor according to the invention.

An oxygen sensor 10 of FIG. 1 according to the invention operates on the known principle of an oxygen concentration cell: the sensor 10 has a tube 12 of an oxygen ion conductive solid electrolyte typified by a zirconia ceramic containing an stabilizing oxide such as calcia. The solid electrolyte tube 12 is closed at one end (this end will hereinafter be referred to also as the front end of the tube 12 and the open end as the rear). The outer surface of the solid electrolyte tube 12 is entirely coated with a porous (permeable to gases) and electron conductive anode electrode layer 14 which is usually of platinum. The inner surface of the solid electrolyte tube 12 is entirely coated with a cathode electrode layer 16 which is similar to the anode electrode layer 14 both in the material and in the structure.

The outer diameter of the solid electrolyte tube 12 is locally enlarged to form an annular ridge or collar 12a between a middle section and the open end of the tube 12. The electrolyte tube 12 is inserted into a tubular metal shell 18 the inner diameter of which is locally enlarged to fit with the collar 12a of the electrolyte tube 12 such that a front end portion of the tube 12 protrudes from the shell 18. The metal shell 18 has on its outside an attachment means such as threads for the attachment of the sensor 10 to, for example, an exhaust pipe in an automotive engine system. This metal shell 18 serves also as an anode conductor. A cup-shaped hood 20 with a number of exhaust gas admitting slots 20a is optionally attached to the shell 18 so as to enclose therein the protruded front end portion of the electrolyte tube 12. The tube 12 and the shell 18 are so shaped as to provide an annular space therebetween over a length from the rear end of the collar 12a to the rear end of the tube. This annular space is filled with a powdery and electrically conductive seal material 22, which is in a closely tamped state. The seal material 22 is usually a powdery mixture of a metal such as copper, iron and/or nickel and a refractory but electrically nonconductive material such as alumina, magnesia and/or talc. Alternatively, either graphite powder or powdered semiconductor glass is used as the seal material 22. To support the seal material 22 and fix the electrolyte tube 12 to the shell 18, a metal ring 24 is forcibly inserted into the rear end portion of the annular space. Another metal ring 24' may tightly be inserted into a middle portion of the annular space to divide the seal material 22 into two blocks when the annular space has a relatively large axial length. The seal material 22 and the rings 24, 24' provide a hermetic seal between the outside of the electrolyte tube 12 and the inside of the shell 18 and contribute also to the assurance of electrical connection between the anode coating 14 and the shell 18.

A rear end portion of the bore of the electrolyte tube 12 is made to have an enlarged diameter with a tapered region at the inside of the collar 12a. A metal tube 26 which has a tapered flange 26a at its one end is inserted into the enlarged rear end portion of the electrolyte tube 12 such that the tapered flange 26a fits with the tapered region of the inside of the electrolyte tube 12 (to be exact, with the cathode coating 16). The metal tube 26 has such a length that its rear end portion remains outside of the bore of the electrolyte tube 12. An annular space formed in the rear of the flange 26a between the cathode coating 16 and the metal tube 26 is filled with a powdery and electrically conductive seal material 22', which is identical with or analogous to the above described seal material 22. The metal rings 28 and 28', with an interval therebetween, are forcibly inserted into the annular space surrounding the metal tube 26 so as to prevent any movement of the metal tube 26, retain the seal material 22' in the annular space, and assure the electrical connection between the cathode coating 16 and the metal tube 26. Thus, the metal tube 26 serves both as a cathode conductor and as a conduit for admitting air as a reference gas into the interior of the electrolyte tube 12. The metal tube 26 has a slot at a region protruded from the electrolyte tube 12, and a jacketed cable wire 30 which serves as the cathode lead of the sensor 10 is inserted into the metal tube 26 from its rear end. The inserted end of the cable 30 is stripped and either welded or soldered to the tube 26 as indicated at 34.

In the above described part, the oxygen sensor 10 is constructed in a known manner. As a primary feature of an oxygen sensor according to the invention, the sensor 10 has a novel plug assembly 40 positioned at a certain distance from the open end of the electrolyte tube 12 with the support of a cap member 42 which is fixed to the rear end of the shell 18. This plug assembly 40 serves the functions of surely protecting the open end of the electrolyte tube 12 and the cathode conductor 26 against splashing of water from the outside, providing an air-admitting passage to the interior of the electrolyte tube 12 and supporting both the cable wire 30 for the cathode and another jacketed cable wire 32 for the anode. (An air admitting passage formed in the plug assembly 40 is only generally indicated at 100 in FIG. 1 for avoidance of complexity, but the passage will fully be understood from the description given hereinafter with reference to FIGS. 3–18.)

The cap member 42 is made of a sheet metal and has a cylindrical shape. The cap member 42 has no aperture in its wall but is grooved at its middle section to provide an annular ridge 42a on the inside. The plug assembly 40 is made up of a plug member 44 which is made of an elastic but moderately hard resin or rubber and a ring-shaped retainer member 46 of either a metal or a hard resin. The plug member 44 is shaped circular in cross section but nonuniform in diameter. In elevation, the plug member 44 has the largest diameter at its one end portion to form a flange 44a and a cylindrical portion of a smaller diameter is formed over a certain length contiguous to the flange 44a. Two axial bores are formed in the plug member 44 to respectively pass the two cable wires 30 and 32 therethrough. A radial ditch 45 is preferably formed on the end face of the flange 44a to extend from the end of one of these two axial bores to the periphery of the flange 44a for the purpose of guiding the anode cable 32 to the inside of the cap member 42 without substantially emerging from the plug member 44. The diameter of the flange 44a substantially equals to the inner diameter of the cap member 42. The ring-shaped retainer member 46 has substantially the same outer diameter as the flange 44a and an inner diameter slightly larger than the outer diameter of the cylindrical portion of the plug member 44. An end portion of the cap member 42 is bent outwards to provide a flange 42b, and the shell 18 has a thin-wall (and enlarged inner diameter) rear end region 18a extending rearwards of the rear end of the electrolyte tube 12 for fixing the cap member 42 to the shell 18 as will later be described. The outer diameter of this flange 42b is larger than the inner diameter of the shell 18 at the front end of the thin-wall region 18a but smaller in the thin-wall region 18a.

The anode cable 32 is stripped at its one end and welded or soldered to the inside of the cap member 42 at a location close to the annular ridge 42a as indicated at 48, while the cathode cable 30 is connected to the cathode conductor 26 as described hereinbefore. Thereafter the cables 30 and 32 are respectively passed through the two bores of the plug member 44. Then the flange 42b of the cap member 42 is inserted into the thin-wall region 18a of the shell 18 to contact with the shoulder formed at the front end of the thin-wall region 18a. A seal ring 50 made of a relatively soft metal such as copper is placed on the outside of the cap member 42, and the thin-end region 18a of the shell 18 is crimped inwards to press the ring 50 against the flange 42b thereby to fix the cap member 42 to the shell 18. Thereafter the plug member 44 is inserted into the cap member 42 by the flange 44a while the cables 30 and 32 are pulled rearwards until the advance of the flange 44a is obstructed by the annular ridge 42a. Then the retainer member 46 is assembled with the plug member 44 to rest on the rear end of the flange 44a, and the free end of the cap member 42 is crimped over the entire periphery to firmly press the retainer member 46 against the plug member 44. Thus the plug assembly 40 is fixed to the cap member 42 and hence to the shell 18.

Preferably, the cables 30 and 32 are covered with a flexible and insulating sheath 52 together with the small diameter portion of the plug member 44 in advance of the attachment of the retainer member 46. When the use of the sheath 52 is intended, the plug member 44 is preferably shaped to have a conical end portion contiguous to the cylindrical portion to be surrounded by the retainer member 46. An example of the sheath 52 is a heat-shrinkable silicone tube. In this case, the sheath 52 is made to shrink and intimately contact with the cables 30, 32 and the plug member 44 by hot air before the placement of the retainer member 46.

FIGS. 2–6 show particulars of the plug assembly 40 as a first example.

A plug member 44 shown in FIGS. 2, 3, 4-a and 4-b is shaped to have a disk flange 144a as one end portion in elevation, a truncated conical portion 144b as the other end portion and a cylindrical middle portion 144c. As described hereinbefore, the flange 144a has a larger diameter than the other portions 144b and 144c and can slidably be received in the cap member 42. Two axial bores 150 and 152 for individually passing the two cables 30 and 32 therethrough are formed near to and parallel to the longitudinal axis of the plug member 144. Preferably, a radial ditch 145 is formed on the end face of the flange 144a to extend from the end of the bore 152 to the periphery of the flange 144a. Two holes 154 and 156 of a small cross-sectional area are formed in the flange 144a parallel to the longitudinal axis of the plug member 144 as seen in FIGS. 3 and 4-a. These two holes 154, 156 are positioned not to intersect the ditch 145 and at the same distance from the axis of the plug member 144, this distance being larger than the radius of the cylindrical portion 144c. It is preferable that these holes 154, 156 are arranged, in plan view, on a diameter of the flange 144a.

A ring-shaped retainer member 146 shown in FIGS. 5 and 6 has the same outer diameter as the flange 144a of the plug member 144 and an inner diameter slightly larger than the diameter of the cylindrical portion 144c. Two holes 158 and 160 of a small cross-sectional area are formed in this member 146 parallel to its longitudinal axis and symmetrically with respect to the same axis, preferably on a diameter of the retainer member 146. In plan view, a circumference containing thereon the two holes 158, 160 is identical with another circumference containing thereon the two holes 154, 156. An annular and shallow recess 162 is formed on one end face of the retainer member 146 along the inner periphery of this end face with such an outer diameter that the two holes 158, 160 open into this recess 162. Preferably, the outer diameter of the retainer member 146 is decreased over a short axial length from the other end face so as to provide a shoulder 164.

Referring to FIG. 2, the plug member 144 and the retainer member 146 are assembled together to constitute a plug assembly 40A such that the cylindrical portion 144c of the plug member 144 is enclosed by the retainer member 146 and that the recessed end face of the retainer member 146 rests on the flange 144a. Preferably a heat-shrinkable sheath tube 52 is applied to the plug member 144 to intimately cover the cylindrical portion 144c prior to the assemblage with the retainer member 146. The provision of the shoulder 164 is convenient to the crimping of the cap member 42 against the retainer member 146. It will be understood that the two holes 154, 156 of the plug member 144 open into the annular recess 162 and that air can be admitted into the interior of the oxygen sensor 10 when this plug assembly 40A is arranged in the sensor 10 as described with reference to FIG. 1. To prevent the intrusion of water into the interior of the sensor 10 through the thus formed air passages, the retainer member 146 is positioned such that the holes 158 and 160 do not overlap either of the holes 154 and 156 in plan view. It is preferable to make the holes 158 and 160 as distant as possible from either of the holes 154 and 156. In other words, it is preferable that each of the holes 158 and 160 in plan view of the plug assembly 40A is circumferentially deviated by about 90° from both of the holes 154 and 156. As the result, each of the air admitting holes 158 and 160 is directly open to the atmosphere but is not directly open to the interior of the cap member 42. Each of the holes 158 and 160 is connected to the holes 154 and 156, which are directly open to the interior of the cap member 42, via arc-shaped channels as part of the annular and shallow recess 162 which lies normal to the holes 154, 156, 158 and 160.

It is possible that water enters the holes 158 and 160 from the outside while the sensor 10 is in use. However, the water does not pass through the holes 154 and 156 because the water is not pressurized and cannot freely flow through any narrow, long and turning channel formed in the plug assembly 40A. The water stagnates in several places within the air passages of the plug assembly 40A and blocks the air passages against further ingress of water. The stagnated water gradually evaporates because the cap member 42 is heated by heat from the exhaust gas through the metal shell 18. The pressure in the interior of the cap member 42 rises due to the heating of the sensor 10 by the exhaust gas, so that the evaporated water is discharged from the air passages into the atmosphere through the holes 158 and 160. Accordingly, the electrolyte tube 12 and the cathode conductor 26 are never wetted with water even when the plug assembly 40A and/or the cap member 42 are splashed with water during, for example, operation of an automobile carrying the sensor 10.

As a natural modification, one of the holes 154, 156 of the plug 144 and/or one of the holes 158, 160 of the retainer 146 may be omitted. On the contrary, the plug 144 and/or the retainer 146 may respectively have three or more air admitting holes. Besides, it is permissible to omit the provision of the annular recess 162 in the retainer 146 and arrange the holes 158, 160 respectively in axial alignment with the holes 154, 156 when these holes 154, 156, 158 and 160 are made quite narrow and long enough to cause the above described stagnation of water therein.

Figure 7:
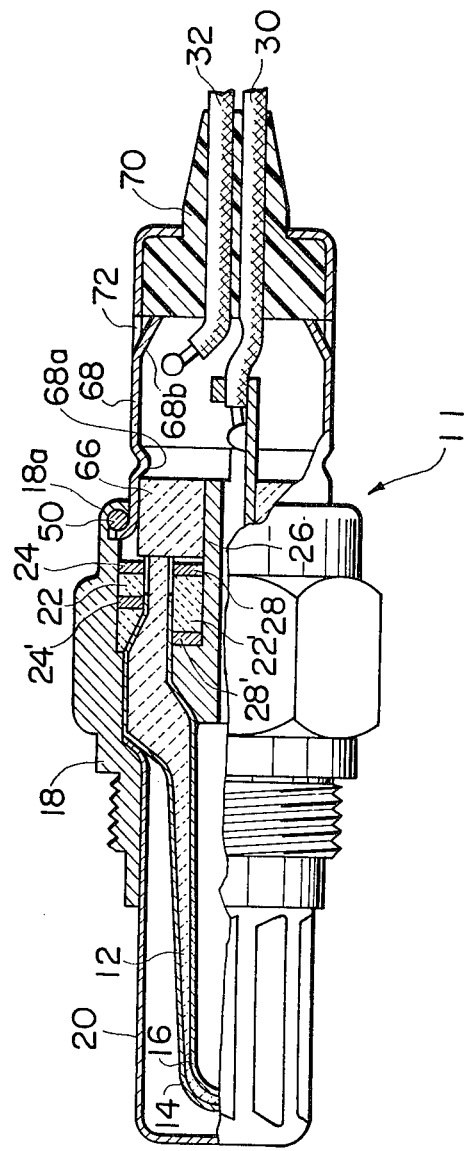
FIG. 7 is a longitudinal sectional view of a conventional oxygen sensor.

For the sake of comparison, FIG. 7 shows a conventional oxygen sensor 11 which is principally similar to the sensor 10 of FIG. 1. This sensor 11 includes an annular ceramic pad 66 which is arranged to intimately cover the rear end face of the electrolyte tube 12. The tubular cathode conductor 26 extends rearwards through the hole of this annular pad 66. A cap member 68 is fixed to the shell 18 in the same manner as the fixing of the cap member 42 to the shell 18 in the sensor 10 of FIG. 1. The inside of the cap member 68 has an annular ridge 68a at a middle section so that the ceramic pad 66 may be pressed against the end face of the electrolyte tube 12 by this ridge 68a when the cap member 68 is fixed to the shell 18. A plug 70 is inserted into a rear end portion of the cap member 68, and the rear end of the cap 68 is circumferentially crimped against a shoulder of this plug 70. The cables 30 and 32 are tightly passed through the plug 70. A plurality of slits indicated at 72 are formed in the wall of the cap 68 at a certain distance from the rear end in a circumferential and spaced arrangement. Each of these slits 72 consists of two linear and spaced portions extending parallel to the longitudinal axis of the cap 68 and a circumferential portion connecting the two linear portions at their ends closer to rear end of the cap 68. A claw 68b is formed by folding inwards the rectangular region surrounded on three sides by each slit 72. The claws 68b support the inserted end of the plug 70. The forming of the claws 68b naturally results in that the slits 72 serve as air inlets to the interior of the cap 68.

When the cap 68 of this sensor 11 is splashed with water, water freely enters the interior of the cap 68 through the opened slits 72. Although the electrolyte tube 12 is protected against water by the ceramic pad 66, the cathode conductor 26 and the welded ends of the cables 30, 32 are easily wetted with water. Accordingly the sensor 11 is liable to suffer a decreased insulation resistance.

A plug assembly 40B of FIG. 8 is different from the plug assembly 40A of FIG. 2 only in that both a plug member 244 and a retainer member 246 have slots on their outer peripheries instead of the air admitting holes 154, 156, 158, 160 in FIGS. 3 and 5. The plug member 244, as shown in FIGS. 9, 10-a and 10-b, is similar to the above described plug member 144 in fundamental shape and diameters. Instead of forming holes in its flange 244a, two narrow and shallow slots 254 and 256 are formed on the cylindrical side surface of the flange 244a parallel to the longitudinal axis of the plug 244. These slots 254, 256 extend over the entire thickness of the flange 244a as seen in FIG. 10-a and are arranged to divide the cylindrical surface into two equal parts. The back end face (conjoining to the cylindrical portion 244c) of the flange 244a is shallowly cut along the outer periphery of this end face such that a back end portion 244d of the flange 244a is slightly smaller in diameter than the remaining portion but yet larger than the cylindrical portion 144c. As the result, the axial slots 254 and 256 terminate at this circumferential cut.

The ring-shaped retainer member 246 of FIGS. 11 and 12 is similar to the retainer 146 of FIGS. 5 and 6 in shape and diameters. Two narrow slots 258 and 260 are formed on the cylindrical outer surface of this retainer 246 to extend parallel to the longitudinal axis of this retainer 246 and divide the outer surface into two equal parts. The depth of these slots 258, 260 from the surface is larger than the depth of the slots 254, 256 of the plug 244.

The retainer 246 is assembled with the plug 244 in such an arrangement that each of the slots 258 and 260 in plan view of the plug assembly 40B is circumferentially deviated by about 90° from both of the slots 254, 256 of the plug 244. In this plug assembly 40B the cut portion 244d of the flange 244a gives an annular groove 262 which serves substantially the same function as the annular recess 162 in the plug assembly 40A of FIG. 2. Accordingly the plug assembly 40B can admit air therethrough but prevents water from freely passing therethrough similarly to the plug assembly 40A when employed in the oxygen sensor 10 of FIG. 1.

For the plug assembly 40B, one of the slots 254, 256 and/or one of the slots may be omitted, or the plug 244 and/or the retainer 246 may respectively have three or more axial slots for admission of air. Besides, it is permissible to omit the cutting of the flange 244a at the portion 244d and arrange the slots 254, 256 respectively in axial alignment with the slots 258, 260 when the slots 254, 256, 258, 260 are sufficiently long.

Figure 13:
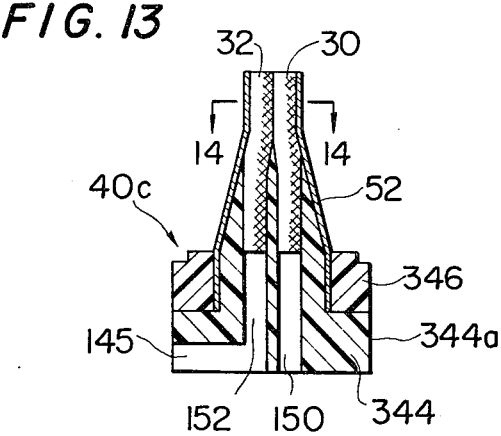
FIG. 13 is a longitudinal sectional view of a still differently constructed plug assembly also as an alternative to the plug assembly of FIG. 2.

Another plug assembly 40C shown in FIG. 13 is different from the plug assemblies 40A and 40B in that an axially straight air admitting passage is formed along two bores for passing therethrough the cables 30 and 32 and that the sheath 52 is utilized to prevent intrusion of water into this air passage.

Figure 15:
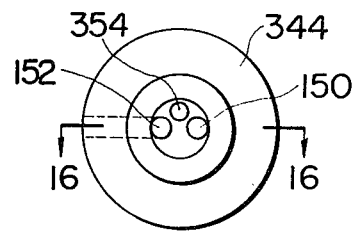
FIGS. 15 and 17 are plan views showing two elements of the plug assembly of FIG. 13, respectively.
Figure 16:
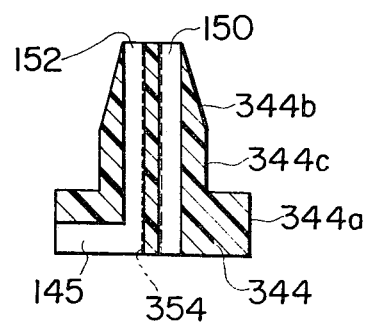
FIGS. 16 and 18 are sectional views respectively taken along the line 16—16 of FIG. 15 and the line 18—18 of FIG. 17.

A plug member 344 shown in FIGS. 15 and 16 is similar to the above described plug 144 in fundamental shape and diameters. Instead of forming holes in its flange 344a, an axial hole 354 of a small cross-sectional area is formed near to and generally parallel to two bores 150 and 152 for the cables 30 and 32. This hole 354 passes through all of the flange 344a, cylindrical portion 344c and truncated conical portion 344b of the plug 344.

Figure 17:
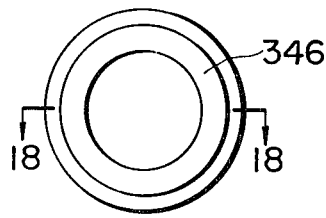
Figure 18:
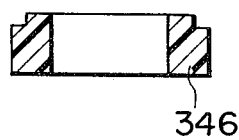

A ring-shaped retainer member 346 of FIGS. 17 and 18 is similar to the retainer 146 in fundamental shape and diameters. There is no need of forming any hole or slot in this retainer 346 for passing air therethrough when the retainer 346 is assembled with the plug 344.

Figure 14:
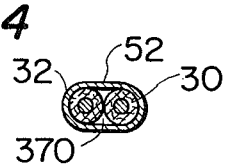
FIG. 14 is a sectional view taken along the line 14—14 of FIG. 13.

Before the assemblage of the retainer 346 with the plug 344, the cables 30 and 32 are individually passed through the bores 150 and 152 of the plug 344, and then the cables 30, 32 and the plug 344, except for its flange 344a, are sheathed in the tubular sheath 52 which is preferably of a heat-shrinkable material as described hereinbefore. After the sheath 52 is shrinked to tightly hold the cables 30 and 32, the retainer 346 is placed on the back end face of the flange 344a to surround the cylindrical portion 344c of the plug 344 with the sheath 52 interposed therebetween. In this state, a narrow space indicated at 370 in FIG. 14 is left along the cables 30 and 32 in the sheath 52 at a portion extending rearward of the plug 344. When this plug assembly 40C is employed in the sensor 10, the interior of the cap member 42 communicates with the atmosphere through the hole 354 and the space 370 since the cables 30 and 32 protrude from the sheath 52 at some distance from the plug assembly 40C for the connection to an external element. The intrusion of water into the interior of the cap member 42 through the hole 354 can easily and completely be prevented by exposing the cables 30 and 32 to the atmosphere (terminating the sheath 52) at a location where the cables 30 and 32 have no chance of being wetted with water. It is possible to omit the use of the sheath 52 even in this plug assembly 40C by making the plug 344 very long and the hole 354 very narrow.

What is claimed is:

1. An oxygen sensor comprising:
   an oxygen ion-conductive electrolyte tube which is closed at one end;
   anode and cathode electrode layers coated on the outer and inner surfaces of said electrolyte tube, respectively;
   a shell surrounding said electrolyte tube;
   a cap member;
   said shell and cap member being arranged so as to permit the flow of gas between the interior of said shell and cap member;
   a plug assembly located in said cap member;
   said plug assembly being provided with first means for permitting the passage of a gas through said assembly thus making it possible for gas to pass from outside to inside the cap member by means of said passage and comprising a plug member, said plug member having a cylindrical portion, a ring-shaped retainer member, said retainer member surrounding a part of said cylindrical portion of said plug member, and said plug member having second means for preventing the passage of unpressurized water from outside said cap member to within said cap member by way of said first means; and
   cables passing through said plug assembly, said cables being in separate electrical contact with said cathode and anode electrode layers respectively.

2. The oxygen sensor as defined by claim 1, wherein said plug member comprises a flange surrounding said cylindrical portion.

3. The oxygen sensor as defined by claim 2, wherein said first means for permitting the passage of gas comprises at least one hole located in said flange and at least one hole located in said ring shaped retainer member.

4. The oxygen sensor as defined by claim 3, wherein said holes are arranged parallel to the main axis of said electrolyte tube.

5. The oxygen sensor as defined by claim 4, wherein each of said at least one hole in said flange is offset circumferentially with respect to each of said at least one hole in said retainer member.

6. The oxygen sensor as defined by claim 5, wherein said circumferential offset is at least 90°.

7. The oxygen sensor as defined by claim 5, wherein said at least one hole in said flange and at least one hole in said retainer member are in gaseous communication with one another by virtue of arc-shaped channels which comprise said second means.

8. The oxygen sensor as defined by claim 7, wherein said retainer member contacts said flange along one of the edges of said retainer member, and said arc-shaped channels are located in said edge of said retainer member which contacts said flange.

9. The oxygen sensor as defined by claim 8 wherein said at least one hole in said retainer member are located between the outer surface and inner surface of said retainer member.

10. The oxygen sensor as defined by claim 9, wherein said at least one hole in said flange are located interiorly of the outer surface of said flange.

11. The oxygen sensor as defined by claim 8, wherein said at least one hole in said retainer member is a slot and is located along the outer edge of said retainer member such that it is partially bordered by the inner wall of said cap.

12. The oxygen sensor as defined by claim 11, wherein said at least one hole in said flange is a slot and is located along the outer edge of said flange such that a portion of said slot is partially bordered by the inner wall of said cap.

13. An oxygen sensor comprising:

an oxygen ion-conductive electrolyte tube which is closed at one end;

anode and cathode electrode layers coated on the outer and inner surfaces of said electrolyte tube, respectively;

a shell surrounding said electrolyte tube;

a cap member;

said shell and cap member being arranged so as to permit the flow of gas between the interior of said shell and cap member;

a plug assembly located in said cap member;

said plug assembly being provided with first means for permitting the passage of a gas through said assembly thus making it possible for gas to pass from outside to inside the cap member by means of said passage; and cables passing through said plug assembly, said cables being in separate electrical contact with said cathode and anode electrode layers respectively and being sheathed in a sheath which permits the passage of a gas through the sheath while preventing the passage of unpressurized water;

wherein said plug assembly comprises two bores in which said cables are separately located, and said means permitting the passage of a gas is a hole, distinct from each of said two bores, said hole being arranged parallel to the major axis of said electrolyte tube and having a small enough diameter so as to prevent the passage of unpressurized water, and wherein said plug assembly comprises a plug member having a cylindrical portion and a flange, said sensor being constructed such that said sheath surrounds said cylindrical portion of said plug member, and said hole, which permits the passage of a gas, extends through said cylindrical portion, and wherein said plug assembly further comprises a retainer member which surrounds said sheathed cylindrical portion of said plug member.

14. An oxygen sensor comprising:

an oxygen ion conductive electrolyte tube which is closed at one end;

anode and cathode electrode layers coated on the outer and inner surfaces of said electrolyte tube, respectively;

a shell surrounding said electrolyte tube;

a cap member;

said shell and cap member being arranged so as to permit the flow of gas between the interior of said shell and cap member;

a plug assembly located in said cap member;

said plug assembly being provided with first means for permitting the passage of a gas through said assembly thus making it possible for gas to pass from outside to inside the cap member by means of said passage; and cables passing through said plug assembly, said cables being sheathed in a sheath so as to permit the passage of a gas through the sheath while preventing the passage of unpressurized water; wherein said plug assembly comprises a plug member and a ring-shaped retainer member arranged around said plug member, said sensor being constructed such that said sheath extends to said plug member and is surrounded by said retainer member.

* * * * *